(12) United States Patent
Dannecker et al.

(10) Patent No.: US 6,506,373 B1
(45) Date of Patent: Jan. 14, 2003

(54) AGENT AND METHOD FOR PERMANENT WAVING

(75) Inventors: Beate Dannecker, Darmstadt (DE); Dirk Lauscher, Ober-Ramstadt (DE); Birgit Schreiber, Lindenfels (DE)

(73) Assignee: Wella Aktiengesellschaft, Darmstadt (DE)

( * ) Notice: Subject to any disclaimer, the term of this patent is extended or adjusted under 35 U.S.C. 154(b) by 0 days.

(21) Appl. No.: 09/600,046

(22) PCT Filed: Nov. 11, 1999

(86) PCT No.: PCT/EP99/08669
§ 371 (c)(1),
(2), (4) Date: Jul. 11, 2000

(87) PCT Pub. No.: WO00/28951
PCT Pub. Date: May 25, 2000

(30) Foreign Application Priority Data

Nov. 14, 1998 (DE) .......................... 198 52 611

(51) Int. Cl.$^7$ ................................. A61K 7/09
(52) U.S. Cl. ...................... 424/70.2; 424/70.1; 424/489; 424/464; 424/401; 132/203; 132/204; 132/205
(58) Field of Search ............................ 424/70.1, 70.11, 424/70.2, 489, 464; 132/204, 205, 203

(56) References Cited

U.S. PATENT DOCUMENTS

| | | | |
|---|---|---|---|
| 2,780,579 A | | 2/1957 | Schwarz |
| 5,051,252 A | | 9/1991 | Schultz |
| 6,074,439 A | * | 6/2000 | De La Mettrie et al. ....... 8/411 |
| 2001/0008031 A1 | * | 7/2001 | Schultz et al. |

FOREIGN PATENT DOCUMENTS

| | | |
|---|---|---|
| EP | 0 448 185 A2 | 9/1991 |
| FR | 2 176 697 A | 11/1973 |
| JP | 52-128239 | 4/1976 |
| JP | 4-112818 | 4/1992 |

OTHER PUBLICATIONS

Neil E. Rigler And Jerome Schimmel: "Cosmetics Science And Technology", Interscience Publishers, Inc, New York, pp. 1066–1067.

International Cosmetic Ingredient Dictionary And Handbook, Seventh Edition, vol. 1, Published By The Cosmetic, Toiletry And Fragrance Association, p. 92, P 1931.

Dictionary Of Antural Products, vol. Two, Chapman & Hall, London Glasgow New York Tokyo Melbourne MADRASPP, 515–516 And 1316.

K. Schrader, Grundlagen Und Rezepturen Der Kosmetika 2–nd Edition, Hutig Buch Verlag Heidelberg 1989.

* cited by examiner

*Primary Examiner*—Thurman K. Page
*Assistant Examiner*—Liliana Di Nola-Baron
(74) *Attorney, Agent, or Firm*—Michael J. Striker

(57) ABSTRACT

The oxidative hair treatment composition is made by mixing several components immediately prior to application on the hair. One component contains dehydroascorbic acid, its derivatives or salts or their mixture, is anhydrous or contains up to 10% by weight of water, and is a powder, granulate or tablet or micro-encapsulated or a suspension and another component is an aqueous, alcoholic or aqueous alcoholic preparation. In order to avoid an unpleasant mercaptan odor and provide a uniform treatment the method for permanently waving hair includes putting the hair into the desired form, treating it with a keratin-reducing agent, and then rinsing it, after which it is treated oxidatively with the above-described oxidative treatment composition and rinsed once again.

18 Claims, No Drawings

AGENT AND METHOD FOR PERMANENT WAVING

This application is a 371 of PCT/EP99/08669, filed Nov. 11, 1999.

BACKGROUND OF THE INVENTION

The present invention relates to an agent in the form of several components, in which dehydroascorbic acid, its derivatives or salts is present in anhydrous, preferably in solid form for carrying out the oxidative post-treatment for the reductive change in keratin fibers, particularly for the permanent waving of hair.

For the reductive change in keratin fibers, the hair is treated initially with a waving agent, which brings about an opening of the disulfide bonds of the hair keratin, and is then brought into the desired shape. Usually, keratin-reducing mercaptan compounds, such as the salts or esters of mercaptocarboxylic acids, are used here as waving agent. Subsequently, the hair is rinsed with water or a suitable intermediate treatment agent. The reduced hair fibers are then treated oxidatively with a fixative. In so doing, the disulfide bonds within the hair keratin are closed. These disulfide bonds determine the permanent durability of the deformation of the hair, especially when the hair is permanently waved or made smooth.

A portion of the disulfide and thiol groups of the hair keratin is oxidized to higher oxidation states of sulfur, especially to cysteic acid, by fixatives based on hydrogen peroxide, peroxide salts or bromates. By these means, the hair keratin is damaged irreversibly. In addition, in the case of peroxide-containing fixatives, the color pigment of the hair (melanin) is partially destroyed. This is associated with a brightening of the hair.

Different fixatives based on disulfides are known, which allegedly do not have these disadvantages.

The Japanese publication 04-112 818 discloses a fixative for permanent waves on the basis of riboflavin and glutathione (as oxidizing agent).

SUMMARY OF THE INVENTION

In the EP publication 0 448 185, a method is claimed for the treatment of keratin material, for which disulfides of the general formula Z—R—S—S—R—Z, in which Z is a water-soluble group, especially amino, R is a divalent group with at least 2 carbon atoms, particularly $C_2$ to $C_{20}$, are used for the reoxidation of reductively obtained sulfhydryl groups. Preferred disulfides are cystamine disulfide and glutathione disulfide.

Disulfide-containing fixatives have the disadvantage that thiols, which have an unpleasant odor, are formed during the fixation step.

The use of dehydroascorbic acid for adjusting the pH of hair conditioning agents to an acidic value, is known from the Japanese publication 52-128 239. In aqueous solution, dehydroascorbic acid is unstable and decomposes within a few hours.

It is an object to avoid the disadvantages with respect to the bleaching effect, the formation of cysteic acid and the mercaptan odor, which occur during the permanent waving of hair, and to do this without affecting the structure of the hair.

Surprisingly, it was found that this objective can be accomplished in an outstanding manner in accordance with claim 1 by an agent for carrying out the subsequent oxidative treatment of hair, which has previously been treated reductively for permanent waving.

Preferably, the fixative is obtained by mixing 2 components immediately (10 seconds to 20 minutes) before use, component 1 containing dehydroascorbic acid, its derivatives or salts or their mixture, in an anhydrous form or with up to 10% by weight of water, as a powder, a granulate or tablet or microencapsulated or as a suspension and component 2 being an aqueous, alcoholic or aqueous alcoholic preparation.

Aside from dehydroascorbic acid, especially its derivatives, such as dehydroisoascorbic acid, bis-dehydroascorbic acid, bis-dehydroisoascorbic acid as well as their salts, such as their alkali and alkaline earth salts, as well as mixtures thereof, are suitable as inventive agents. Especially preferred are dehydroascorbic acid or bis-dehydroascorbic acid or mixtures thereof.

The ready-for-use fixative preferably contains 0.1 to 20% by weight, preferably 0.5 to 10% by weight and especially 1 to 5% by weight of dehydroascorbic acid or bis-dehydroascorbic acid or its derivatives or its salts or a mixture thereof.

It is especially preferred if the fixative contains 1 to 5% by weight of dehydroascorbic acid or bis-dehydroascorbic acid or mixtures thereof.

Optionally, the fixative may additionally contain conventional oxidizing agents, such as hydrogen peroxide, peroxide salts or bromates. If these are present in liquid form, they are contained in the liquid component.

The pH of the ready-for-use fixative ranges form 1.5 to 10 and preferably from 2 to 8, 2.5 to 7.5 being particularly preferred. The pH. is adjusted with conventional alkalizing materials and buffering materials, such as ammonia, alkali hydroxides, alkali carbonates, alkali hydrogen carbonates, citrate buffer, phosphoric acid and its salts, citrate acid and its salts and, in particular, ascorbic acid and its salts.

The ready-for-use fixative can be present in the form of an aqueous solution or of an emulsion as well as in thickened form on an aqueous basis, particularly as a cream, gel or paste. Preferably, the dehydroascorbic acid, its derivatives or salts or their mixture are used in aqueous or in aqueous alcoholic solution.

Aside from dehydroascorbic acid, it's derivatives or its salts or their mixture, the ready-for-use fixative may also contain additives, which are customary in cosmetic preparations for the hair (compare K. Schrader, Grundlagen und Rezepturen der Kosmetika (Cosmetic Fundamentals and Formulations) $2^{nd}$ edition, Huthig-Verlag, Heidelberg, 1989). These include swelling and penetration materials, such as urea, 2-pyrrolidone, 1-methyl-2-pyrrolidone and dipropylene glycol monomethyl ether, as well as peroxide stabilizers, such as aromatic sulfonic acids, hydrochloric acid, sulfuric acid, phosphoric acid, pyro- or polyphosphoric acids, acidic salts, strong acids, ascorbic acid, oxalic acid, malonic acid, benzoic acid, salicylic acid, citric acid, tannic acids, paraformaldehyde, 4-acetamido-phenol, phenol, thymol or alpha-bisabolol.

Furthermore, the fixative may contain wetting agents and emulsifiers from the group of anionic, nonionic, cationic and amphoteric or zwitterionic surface active agents. Suitable agents are, in particular, a) anionic surface active agents, such as alkali, alkaline earth, ammonium or alkanolamine salts of alkyl sulfonates, alkyl sulfates and alkyl ether sulfates, such as sodium lauryl alcohol diglycol ether sulfate, sodium or triethanolamine salts of alkyl sulfates with 12 to 18 and preferably 12 to 14 carbon atoms, the sodium or triethanolamine salts of lauryl or tetradecyl ether sulfate, the disodium salt of the sulfosuccinic half ester of alkanolamides, soaps and polyether carboxylic acids;

b) nonionic surface active agents, such as ethoxylated fatty alcohols with 12 to 18 carbon atoms, such as lauryl, tetradecyl, cetyl and stearyl alcohol, ethoxylated with up to 40 moles of ethylene oxide per mole of fatty alcohol, alone or in a mixture, ethoxylated lanolin alcohols, ethoxylated lanolin, ethoxylated alkylphenols with 8 to 30 carbon atoms in the alkyl group and 1 to 10 ethylene oxide units in the molecule, fatty acid alkanolamides as well as ethoxylated sorbitol fatty acid esters;

c) cationic surface active agents, such as dilauryldimethylammonium chloride, chlorides or bromides of alkyldimethylbenzylammonium salts, alkyltrimethylammonium salts such acetyltrimethylammonium chloride or bromides, tetradecyltrimethylammonium chloride or bromides, alkyldi-methylhydroxyelhylammonium chlorides or bromides, dialkyldimethylammonium chlorides or bromides, alkylpyridinium salts, such as lauryl- or cetylpyridinum chloride, alkylamidoethyltri-methylammonium ether sulfates, compounds with a cationic character, such as amine oxides, for example, alkyldimethylamine oxides or alkylaminoethyldimethylamine oxides and d) amphoteric or zvitterionic surface active agents, such as carboxyl derivatives of imidazols, N-alkylbetaines, N-alkylamidobetaines, N-alkylsulfobetaines, N-alkylamino-propionates, alkyldimethylcarboxymethylammonium salts with 12 to 18 carbon atoms, as well as fatty acid alkylamidobetaines, such as fatty acid amidopropyldimethylamino acetic acid betaine.

Of course, the fixative may contain all additives, customary for such agents, such as thickening agents, for example, kaolin, bentonite, fatty acids, higher molecular weight fatty alcohols, starch, polyacrylic acid and their derivatives, cellulose derivatives, alginates, Vaseline or parafin oil, dyes, opacifiers, such as polyethylene glycol esters, or alcohols such as ethanol, propanol and isopropanol, solubilizers, buffers, perfume oils, hair conditioning or hair care components, such as lanolin derivatives, cholesterol, pantothenic acid, protein derivatives and hydrolysates, betaine, pro-vitamins and vitamins, as well as plant extracts.

For producing the ready-for-use fixative, the components of the cosmetic preparation are used in amounts customary for this purpose. For example, wetting agents and emulsifiers are used in concentrations of 0.2 to 30% by weight, alcohols in a concentration of 1 to 80% by weight, hair conditioning or hair care components in a concentration of 0.1 to 10% by weight, and thickening agents in concentrations of 0.1 to 25% by weight, based on the ready-for-use fixative.

Solid additives and additives, compatible with dehydroascorbic acid, may be contained together with the dehydroascorbic acid in component 1, while the remaining additives are contained in the liquid component 2.

The application temperature of the ready-for-use fixative ranges from 10° C. to 60° C. and preferably from 20° C. to 55° C. and especially from 30° C. to 50° C. The duration of action ranges from 1 to 45 minutes, preferably from 3 to 25 minutes and especially from 5 to 15 minutes.

The inventive fixative in component 1, based on dehydroascorbic acid, preferably is anhydrous. In this connection, anhydrous does not mean that any trace of water must be excluded. In the raw materials used, the water of crystallization or traces of moisture contained should merely not exceed a total of 10% by weight, preferably of 4% by weight and especially of 1% by weight, based on component 1.

The dehydroascorbic acid, its derivatives or its salt or its mixture is used in component 1 alone or as a mixture with the additives, conventionally used in cosmetics, in an anhydrous medium, preferably as a dust-free powder, granulate or as a tablet. When introduced into the suitable medium of component 2, which preferably represents an aqueous or aqueous, alcoholic solution, a ready-for-use fixative is obtained, which contains 0.1 to 20% by weight, preferably 0.5 to 10% by weight and especially 1 to 5% by weight of dehydroascorbic acid, its derivatives or salts or their mixture.

A further object of the present invention is a method for permanent hair waving, for which the hair, before and/or after it is brought into the desired shape, is treated with a keratin-reducing, permanent waving agent, rinsed, then treated oxidatively with a fixative, rinsed, subsequently styled and then dried, wherein the fixative, described above, is used for the oxidative treatment. Preferably, rinsing is carried out with water.

In the case of a special embodiment of the inventive method, the hair is first treated with the keratin-reducing permanent waving agent, the permanent waving agent is rinsed out after a period of time, subsequently the hair is treated with the fixative, which is described above and based on dehydroascorbic acid, its derivatives or salts as oxidizing agent (pre-fixed) and then treated with a fixative based on hydrogen peroxides or bromate (post-fixation). It is particularly advantageous if the fixative, for the post-fixation, has a lesser concentration of oxidizing agent than is customary for such fixatives; for example, the concentration of hydrogen peroxide is only 0.1 to 1% by weight and of the bromate only 1 to 5% by weight.

For the inventive method, the hair is washed, massaged with a towel, optionally pre-moistened with a portion of the keratin-reducing permanent waving agent, divided into individual strands and wound on curlers. Depending on whether permanent waving is desired or the hair is to be straightened, the diameter of the curler is either about 5 to 13 mm or about 15 to 35 mm. An amount of agent, adequate for permanent waving, is subsequently applied on the hair in curlers. The total amount of agent, required for the permanent waving, generally is about 80 to 100 g.

The permanent waving agents, which can be used for the inventive method, usually contain keratin-reducing compounds, such as certain mercapto compounds, particularly thioglycolic acid, thioglycerin, cysteine, cysteamine as well as salts or esters of mercapto carboxylic acids. These permanent waving agents contain the keratin-reducing compounds in amounts, customary for such agents. For example, the ammonium salts of thioglycolic acid or thiolactic acid are contained in an amount of about 2 to 12 percent by weight. The pH of these permanent waving agents generally is about 7 to 11. The pH preferably is adjusted with ammonia, monoethanolamine, ammonium carbonate or ammonium hydrogen carbonate. When adjusting the permanent waving agent to an acidic pH of, for example, 6.5 to 6.9, preferably esters of mercaptocarboxylic acids, such as monothioglycolic acid glycol esters or glycerin esters are used in a concentration of about 2 to 25% by weight.

The permanent waving agents furthermore may contain all additives, customary for such agents, such as swelling materials, penetration materials, thickening agents, wetting agents and emulsifiers, alcohols, solubilizers, stabilizers, dyes, perfume oils as well as hair-conditioning or hair care components. The additives, named above, are used in amounts customary for such purposes. For example, the wetting agents and emulsifiers are used in concentrations of about 0.2 to 30% by weight, while the thickeners may be contained in an amount of about 0.1 to 25% by weight in the permanent waving agent.

The permanent waving agent, used in the inventive method, may be present in the form of an aqueous solution or emulsion, as well as in thickened form on an aqueous basis, especially as a cream, gel or paste or in the form of an aerosol foam.

After a period of action, which is sufficient for permanent waving and depends on the nature of the hair, the pH and the effectiveness of the permanent waving agent as well as on the application temperature, and amounts to 5 to 45 minutes (5 to 30 minutes with heat; 20 to 45 minutes without heat), the hair is rinsed with water and then treated oxidatively with 50 g to 350 g and preferably with 80 g to 200 g of the ready-for-use fixative described above.

After the fixative has been allowed to act for 1 to 45 minutes, preferably 3 to 25 minutes and especially 5 to 15 minutes, the curlers are removed and the unrolled hair, if necessary, is treated once again oxidatively with the fixative. The hair is then rinsed preferably with water, styled and dried.

The hair, so treated, has a uniform transformation, which is increasingly durable after repeated such permanent wave treatments. In contrast to hair, which was fixed with peroxide and has a clearly detectable shift in coloring the direction of red and yellow (degree of brightening), the values for the fixative, use pursuant to the invention, lie within the range of un-treated hair strands. In addition, the cysteic acid content of the hair, so treated, is clearly less than that of hair, which was treated with a fixative based on hydrogen peroxide and bromate. In addition, the oxidation with the fixative, described here, does not result in an unpleasant mercaptan odor.

Comparison Experiments

Comparison of the Hair Damage when Dehydroascorbic Acid is Used and when Peroxide and Bromate are Used The outstanding results, achieved with the inventive agent, are illustrated by the comparison experiments described in the following.

The measured values ($\mu$moles/g) of cystine and cysteic acid, as well as the tear strengths (bundle tensile strength (N)) of hair strands, which were permanently waved 3 and 6 times and treated with a freshly prepared dehydroascorbic acid solution, a customary hydrogen peroxides fixative and a customary bromate fixative, were compared.

In each case 2 to 3 untreated and therefore undamaged hair strands (consisting in each case of 100 hairs with a length of exactly 16.5 cm) from central European hair were wound wet on standard spiral curlers (having an internal diameter of 3 mm) and, after conditioning in a room to having a temperature of 20 C. and a relative humidity of 65%, were treated with a conventional commercial permanent waving solution (thioglycolic acid content of 10% by weight with a pH of 8.2). The amount of permanent waving liquid was calculated from the ratio 1:1.2 (1 g of hair to 1.2 g of permanent waving liquid). The amount of 1.2 ml to 1 g of hair corresponds to an amount of 50 ml of permanent waving solution per head with an average weight of about 30 g of hair per head. This solution was allowed to act for 15 minutes; the temperature of the reducing agent acting was 50° C. The permanent waving agent, based on thioglycolic acid, was rinsed out well with water (2 to 3 minutes). Subsequently, the hair strands were in each case moistened intensively with the respective ready-for-use fixative. This procedure was repeated three or six times, in that the strands, after each treatment, was suspended for six hours in the water bath.

The following solutions were used as fixative:

A 2.4% aqueous solution based on hydrogen peroxide (adjusted with phosphoric acid to a pH of 2.5), a 12% aqueous sodium bromate solution (adjusted with sodium phosphate to a pH of 6.4) and a freshly prepared 2.5% aqueous solution of sodium dehydroascorbate (adjusted with sodium hydroxide solution to a pH of 5.6).

The fixative was applied as a rinsing fixative. The amount of fixative corresponds approximately to 80 to 100 ml per 30 g of hair.

Information concerning the advantages of the inventive fixation over the customary fixatives based on hydrogen peroxide and bromate is provided by the cystine and cysteic acid values in $\mu$moles/g, which were obtained by amino acid analysis, and by the determination of the tensile strength of the bundles. The tensile strength of the bundles, which are a measure of the preservation of the hair, were determined using individual strands of hair.

Permanently waved hair strands were used for determining the tensile strength of individual hair. In each case, 20 hairs were taken from the strands and squeezed with a press in small pre-manufactured metal sleeves. Subsequently, the diameters of the hairs were measured and their tensile strengths was determined using stress-strain equipment with turntables.

TABLE

Average values of Cystine Content and Cysteic Acid Content from 3 Strands and Bundle Tensile Strengths from 20 Individual Hairs

| Fixative | Number of Permanent Wave Treatments | Cystine ($\mu$moles/g) | Cysteic Acid ($\mu$moles/g) | Bundle Tensile Strength (N) |
|---|---|---|---|---|
| Peroxide | 3 | 541 | 218 | 7.7 |
| Peroxide | 6 | 429 | 321 | 6.9 |
| Bromate | 3 | 541 | 122 | 9.3 |
| Bromate | 6 | 473 | 213 | 7.2 |
| Dehydroascorbic Acid | 3 | 570 | 35 | 8.1 |
| Dehydroascorbic Acid | 6 | 546 | 51 | 8.3 |

As is evident from the Table, the cystine contents, in the case of all fixatives, are higher in hair permanently waved three times than in hair permanently waved six times. This is explained by the repeated reduction of the keratin of the hair. After a three-fold treatment, the cysteic acid content of hair fixed with peroxide is similar to that fixed with bromate. It is striking that the cysteic acid values, which are a measure of the oxidative damage to the hair, of the hair fixed with dehydroascorbic acid correspond approximately to the blank value of 41 $\mu$moles/g for the cysteic acid content of strands, which have not been permanently waved. Consequently, there is no oxidative damage when dehydroascorbic acid is used. The bundle tensile strength of the strands, fixed with dehydroascorbic acid, are approximately the same after three treatments and after six treatments, so that dehydroascorbic acid is an oxidizing agent, which shows no increase in hair damage even when used repeatedly.

The following examples are given in order to describe the inventive method accurately.

In these examples, the hair was treated reductively in each case in the following manner:

Three to four un-treated and, with that, not previously damaged strands of hair (consisting in each case of 100 hairs with a length of precisely 16.5 cm) from a medium brown central European hair were wound onto standard spiral curlers with an internal diameter of 3 mm and, after being conditioned at 20° C. and a humidity of 65%, treated with a conventional, commercial permanent waving solution, containing 10% by weight of thioglycolic acid and having a pH of 8.2. The amount of permanent waving solution applied was calculated from the ratio of 1:1.2 (1 g of hair to 1.2 ml of permanent waving liquid). The amount of 1.2 ml for about 1 g of hair corresponds to an amount of 50 ml of permanent waving solution per head with an average weight of about 30 g of hair per head. The solution was allowed to act for 15 minutes. The reducing agent acted at a temperature of 50° C.

EXAMPLE 1

At the end of the period of action, the excess permanent waving solution was rinsed out with water and the fixing solution was then applied with a sponge. The fixing solution is prepared 2 minutes before use by dissolving component 1 in component 2.

| | Component 1 |
|---|---|
| 5.00 g | bis-dehydroascorbic acid, anhydrous powder |
| | Component 2 |
| 3.75 g | sodium lauryl alcohol diglycol ether sulfate |
| 91.25 g | water |

The pH of the ready-for-use fixative is adjusted to a value of 3.5 with a 25% aqueous ammonia solution.

The hair is fixed for 30 minutes at 22° C. and subsequently rinsed with water. The curlers are then removed and the hair is rinsed with lukewarm water. Finally, the hair is styled and then dried.

The hair, so treated, exhibits a good a general state, is not brightened and is free of any disturbing mercaptan odor.

EXAMPLE 2

As in example 1, the hair is treated with a fixing solution, prepared one minute before use from components 1 and 2 below.

| | Component 1 |
|---|---|
| 5.00 g | dehydroascorbic acid, anhydrous powder |
| | Component 2 |
| 0.5 g | ethoxylated fatty alcohol sulfate |
| 0.2 g | perfume oil |
| | citrate buffer to a pH of 6.0 |
| to 100.00 g | water |

The hair, so treated, showed a good transformation and a durability, is not brightened and is free of disturbing mercaptan odor.

EXAMPLE 3

As in example 1, the hair is treated with a fixing solution, prepared three minutes before use from components 1 and 2 below.

| | Component 1 |
|---|---|
| 2.5 g | dehydroascorbic acid, anhydrous powder |
| | Component 2 |
| 1.0 g | dimethylaminoethyl methacrylate, 75% quaternized with dimethyl sulfate |
| 0.6 g | fatty acid amidopropyl dimethylaminoacetic acid betaine |
| 0.5 g | lauryldimethylamine oxide |
| 0.5 g | citrate buffer |
| | sodium hydroxide to a pH of 5.6 |
| to 100.00 g | water |

The hair, so treated, is in a good state, is not brightened and is free of disturbing mercaptan odor.

EXAMPLE 4

At the conclusion of a treatment of the hair with the permanent waving agent based on thioglycolic acid, the hair is rinsed with water and a fixative, prepared ready-for-use from the following components 1 and 2 shortly before the application, is applied with a sponge.

| | Component 1 |
|---|---|
| 3.0 g | bis-dehydroascorbic acid as a tablet |
| | Component 2 |
| 0.30 g | castor oil, ethoxylated with 40 moles of ethylene oxide |
| 0.37 g | octylphenol, ethoxylated with 20 moles of ethylene oxide |
| 0.10 g | alpha-bisabol |
| to 100.00 g | water |

Components 1 and 2 are stirred together 5 minutes before use and the mixture obtained is diluted with 4 L of water.

At the conclusion of a treatment of the hair with the permanent waving agent based on thioglycolic acid, the hair is rinsed with water. The hair is then rinsed for 5 minutes with the ready-for-use fixative described above, using a recirculating pump device. After the curlers are removed, the hair is rinsed with water, styled and then dried. A well waved to hair is obtained.

EXAMPLE 5

The hair is reduced as described above. After being rinsed with water, the hair is fixed as follows:

The following composition is suitable for "pre-fixing and rapidly fixing" in combination with a fixative based on hydrogen peroxide.

Pre-fixative

| | Component 1 |
|---|---|
| 1.50 g | dehydroascorbic acid, powder |
| | Component 2 |
| 1.00 g | nonoylphenol polyglycol ether |
| 0.10 g | cationic polymer (CTFA: Polyquaternium-10) |

-continued

| | |
|---|---|
| 0.20 g | perfume |
| | citrate buffer to adjust the pH to a value of 5.0 |
| to 100 g | water |

Component 1 is dissolved 1 to 30 seconds before use in component 2, which has been heated to 50° C.

The final fixing takes place with the following composition:

| | |
|---|---|
| 0.90 g | hydrogen peroxide |
| 0.02 g | phenacetin |
| 0.10 g | perfume |
| 2.00 g | sodium lauryl ether sulfate |
| | phosphoric acid to adjust the pH to a value of 3.5 |
| to 100 g | water |

At the conclusion of a treatment with the permanent waving agent based on a thioglycolic acid, the hair is rinsed with water and then treated with the pre-fixing agent, described above, for 10 minutes (sponge application). Subsequently, the final fixation is applied and allowed to act for five minutes. After the removal of the curlers, the hair is rinsed with water, styled and a dried.

The hair, so treated, is well curled, not brightened and free of disturbing mercaptan odor.

EXAMPLE 6

| | Component 1 |
|---|---|
| 4.0 g | bis-dehydroascorbic acid, anhydrous powder |
| | Component 2 |
| 0.1 g | perfume oil |
| 96.0 g | water |

Component 1 is dissolved 20 seconds before use in component 2. The pH of the ready-for-use preparation is 2.2. The temperature of the ready-for-use preparation was adjusted to 45° C.

At the conclusion of a treatment with the permanent waving agent based on thioglycolic acid, the hair is rinsed with water and then rinsed for 10 minutes at 45° C. with the above described fixative using a recirculating pump device with a temperature control. After removal of the curlers, the hair is rinsed with water, styled and a dried.

The hair, so treated, is not brightened and is free of disturbing mercaptan odor.

What is claimed is:

1. An oxidative hair treatment composition comprising from 2.5 to 10 percent by weight of at least one active ingredient, said at least one active ingredient being selected from the group consisting of dehydroascorbic acid, dehydroisoascorbic acid, bis-dehydroascorbic acid, bis-dehydroisoascorbic acid, salts thereof and mixtures thereof, and wherein said oxidative hair treatment composition is made by mixing a first component with a second component immediately prior to application to hair to be treated;

wherein said first component consists of an anhydrous powder, granulate, tablet or micro-encapsulated product containing said at least one active ingredient in an anhydrous form or with up to ten percent by weight water and said second component comprises an aqueous, aqueous/alcoholic or alcoholic cosmetic preparation containing at least one cosmetic additive ingredient.

2. The oxidative hair treatment composition as defined in claim 1, wherein said at least one active ingredient consists of said bis-dehydroascorbic acid.

3. The oxidative hair treatment composition as defined in claim 1, containing from 2.5 to 5 percent by weight of said at least one active ingredient.

4. The oxidative hair treatment composition as defined in claim 1, wherein said first component contains said at least one active ingredient in anhydrous form or with up to 10 percent by weight water.

5. The oxidative hair treatment composition as defined in claim 1, wherein said first component is mixed with said second component from 10 seconds to 20 minutes prior to application to the hair.

6. The oxidative hair treatment composition as defined in claim 1, in the form of a solution having a pH of 2.5 to 7.5

7. A multi-component kit for oxidative treatment of hair comprising a first component and a second component for mixing with said first component to provide an aqueous, aqueous/alcoholic or alcoholic fixative composition, said aqueous, aqueous/alcoholic or alcoholic fixative composition comprising from 2.5 to 10 percent by weight of at least one active ingredient, said at least one active ingredient being selected from the group consisting of dehydroascorbic acid, dehydroisoascorbic acid, bis-dehydroascorbic acid, bis-dehydroisoascorbic acid, salts thereof and mixtures thereof;

wherein said first component consists of an anhydrous powder, granulate, tablet or micro-encapsulated product comprising said at least one active ingredient in an anhydrous form or with up to ten percent water; and wherein said second component comprises an aqueous, aqueous/alcoholic or alcoholic cosmetic preparation containing at least one cosmetic additive ingredient.

8. The multi-component kit as defined in claim 7, wherein said first component is said anhydrous powder and consists of said bis-dehydroascorbic acid.

9. A method for permanently waving of hair, said method comprising the steps of:

a) bringing the hair into a desired shape;

b) applying a keratin-reducing composition to the hair and allowing the keratin-reducing composition to act on the hair for a period of action sufficient for the permanent waving;

c) rinsing the hair after the applying and allowing of step b);

d) mixing a first component with a second component to form an oxidative hair fixing composition containing from 1 to 10 percent by weight of at least one active ingredient immediately prior to application of the oxidative hair fixing composition to the hair, said at least one active ingredient being selected from the group consisting of dehydroascorbic acid, dehydroisoascorbic acid, bis-dehydroascorbic acid, bis-dehydroisoascorbic acid, salts thereof and mixtures thereof; and wherein said first component consists of an anhydrous powder, granulate, tablet or micro-encapsulated product containing said at least one active ingredient in an anhydrous form or with up to ten percent water, and wherein said second component comprises an aqueous, aqueous/alcoholic or alcoholic cosmetic preparation containing at least one cosmetic additive ingredient;

e) after the rinsing of step c), applying said oxidative hair fixing composition to the hair and allowing said oxidative hair fixing composition to act on the hair for a time sufficient for fixing of the hair in the desired shape; and f) after the applying and the allowing of step e), rinsing the hair again.

10. The method as defined in claim 9, wherein during said applying of the oxidative hair fixing composition to the hair and said allowing, said oxidative hair fixing composition has an application temperature of from 30° C. to 50° C.

11. The method as defined in claim 9, wherein said at least one active ingredient consists of said bis-dehydroascorbic acid.

12. The method as defined in claim 9, wherein said oxidative hair fixing composition contains from 2.5 to 5 percent by weight of said at least one active ingredient.

13. The method as defined in claim 9, wherein said first component is mixed with said second component from 10 seconds to 20 minutes prior to applying said oxidative hair fixing composition to the hair.

14. The method as defined in claim 9, wherein said oxidative hair fixing composition is in the form of a solution having a pH of from 2.5 to 7.5

15. A method for permanently waving hair, said method comprising the steps of:

a) bringing the hair into a desired shape;

b) applying a keratin-reducing composition to the hair and allowing the keratin-reducing composition to act on the hair for a period of action sufficient for the permanent waving;

c) rinsing the hair after step b);

d) mixing a first component with a second component to form an oxidative pre-fixing composition containing from 1 to 10 percent by weight of at least one active ingredient immediately prior to application of the oxidative pre-fixing composition to the hair, said at least one active ingredient being selected from the group consisting of dehydroascorbic acid, dehydroisoascorbic acid, bis-dehydroascorbic acid, bis-dehydroisoascorbic acid, salts thereof and mixtures thereof; and wherein said first component consists of an anhydrous powder, granulate, tablet or micro-encapsulated product containing said at least one active ingredient in an anhydrous form or with up to ten percent water, and wherein said second component comprises an aqueous, aqueous/alcoholic or alcoholic cosmetic preparation containing at least one cosmetic additive ingredient;

e) after the rinsing of step c), applying said oxidative pre-fixing composition to the hair and allowing said oxidative pre-fixing composition to act on the hair for a time sufficient for pre-fixing the hair; and f) after the pre-fixing of the hair of step e), treating of the hair with an oxidative post-fixing composition for post-fixing the hair, said oxidative post-fixing composition containing from 0.1 to 1 percent by weight of hydrogen peroxide or from 1 to 5 percent by weight of bromate as oxidizing agent.

16. The method as defined in claim 15, wherein said at least one active ingredient consists of said bis-dehydroascorbic acid and said first component is said anhydrous powder.

17. The method as defined in claim 15, wherein said oxidative pre-fixing composition contains from 1 to 5 percent by weight of said at least one active ingredient.

18. The method as defined in claim 15, wherein said oxidative pre-fixing composition is a prefixing solution that has a pH of 2.5 to 7.5.

* * * * *